United States Patent [19]

Demaison et al.

[11] Patent Number: 4,599,218
[45] Date of Patent: Jul. 8, 1986

[54] CAPTURE BOX FOR PREDICTING HYDROCARBON POTENTIAL OF AN EARTH FORMATION UNDERLYING A BODY OF WATER

[75] Inventors: Gerard J. Demaison, Orinda; Isaac R. Kaplan, Sherman Oaks, both of Calif.

[73] Assignee: Chevron Research Company, San Francisco, Calif.

[21] Appl. No.: 599,836

[22] Filed: Apr. 13, 1984

Related U.S. Application Data

[63] Continuation of Ser. No. 353,760, Mar. 1, 1982, abandoned.

[51] Int. Cl.[4] .............................................. G01N 33/24
[52] U.S. Cl. ....................................... 422/61; 422/80; 422/89

[58] Field of Search ................ 436/29, 141, 155, 158, 436/161, 175, 59; 422/61, 78, 80, 89; 206/349; 312/208, 209

[56] References Cited

U.S. PATENT DOCUMENTS

| | | | |
|---|---|---|---|
| 1,910,236 | 5/1933 | Butler | 422/61 |
| 2,393,674 | 1/1946 | Zaikowsky | 436/141 X |
| 3,428,432 | 2/1969 | Staunton et al. | 422/78 |
| 3,834,122 | 9/1974 | Allison et al. | 436/29 |
| 3,982,896 | 9/1976 | Keisling et al. | 422/61 X |
| 4,325,907 | 4/1982 | Dembicki et al. | 422/89 X |

*Primary Examiner*—Arnold Turk
*Attorney, Agent, or Firm*—H. D. Messner; Edward J. Keeling

[57] ABSTRACT

The present invention provides for on-site capture of carbonaceous gas at sea, for isotopic examination. A capture box is utilized to provide trapping, stripping and combustion of a gas stream to permit methane analysis.

2 Claims, 5 Drawing Figures

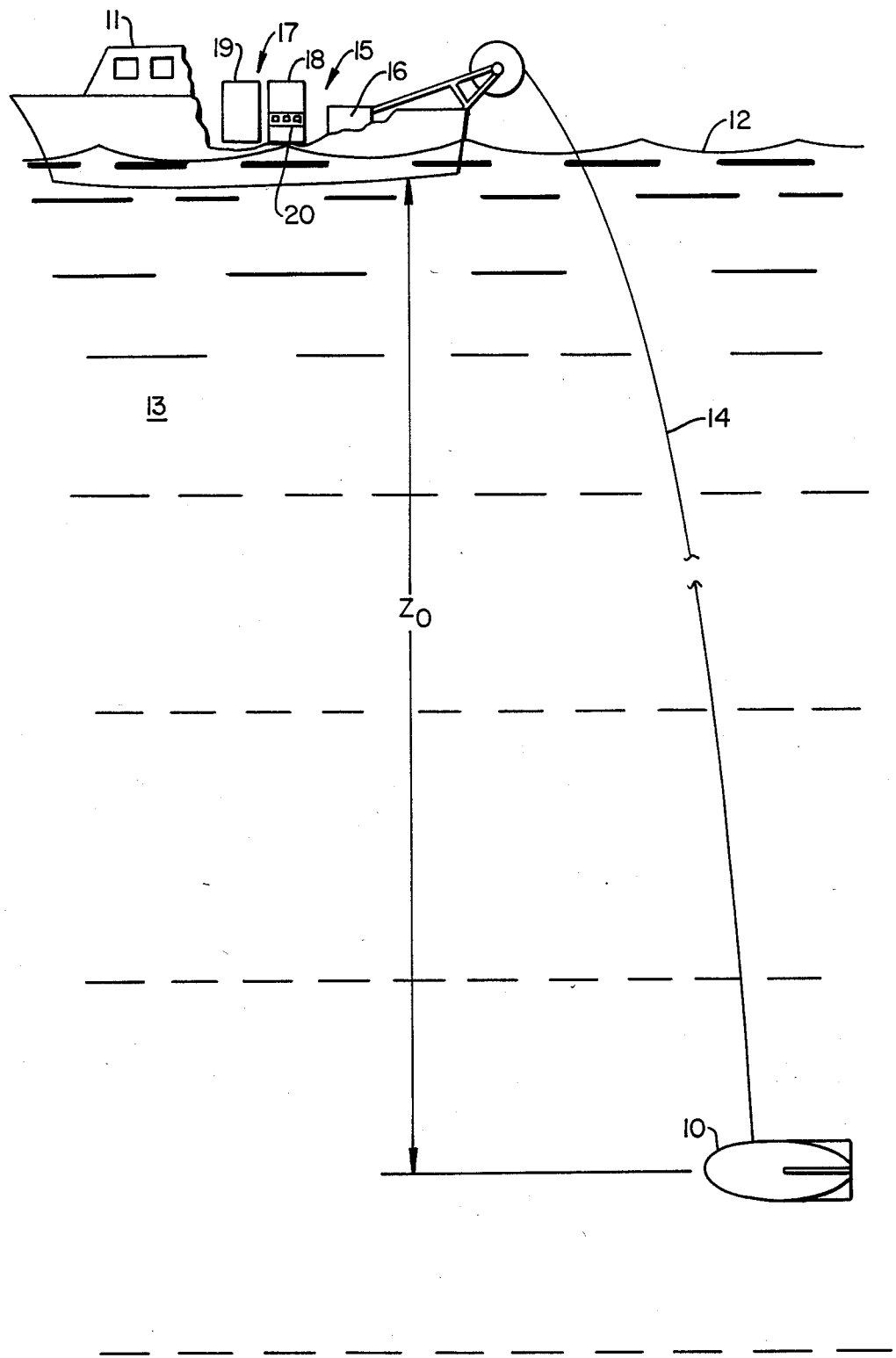
FIG._1.

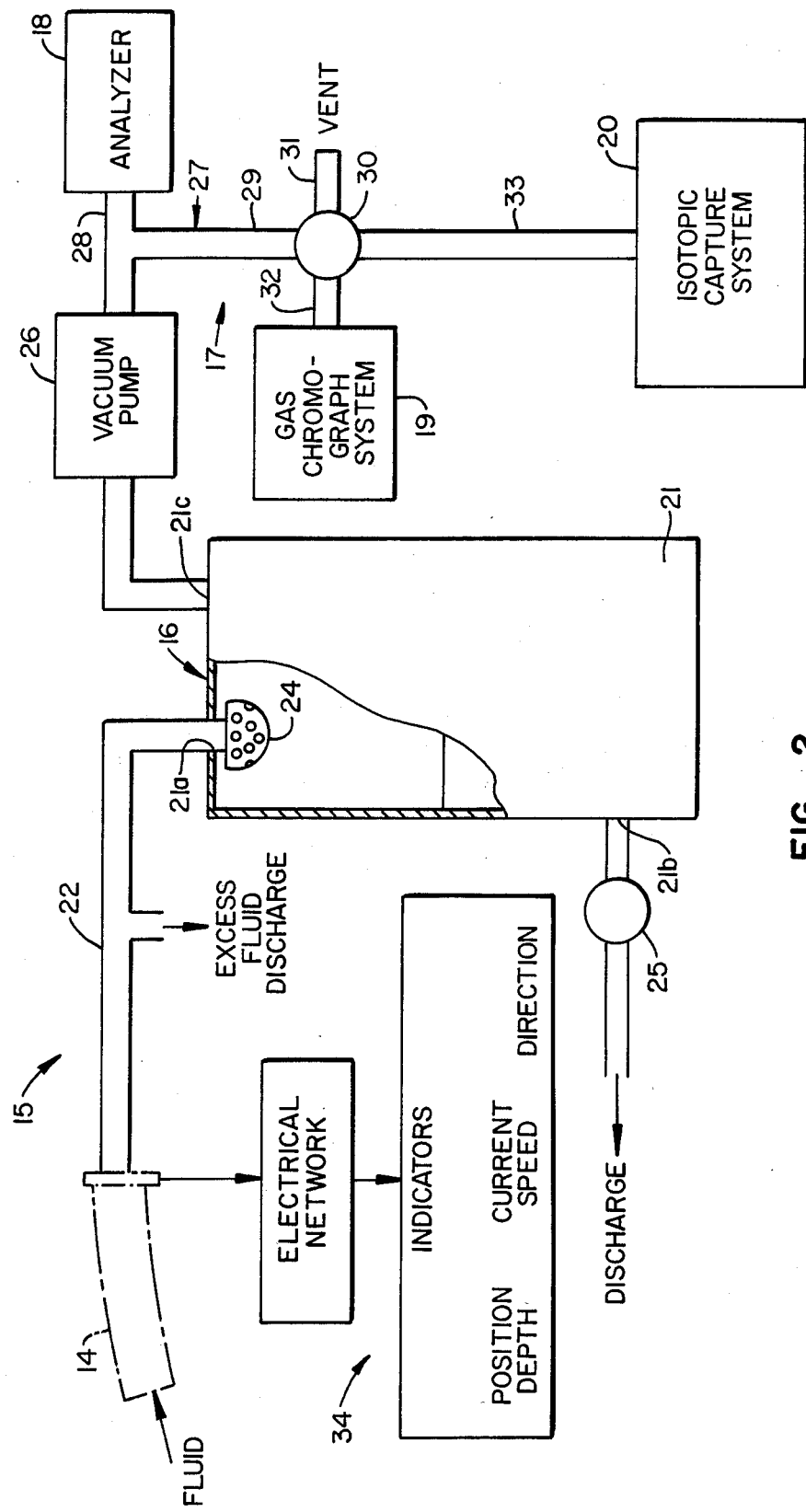
FIG._2.

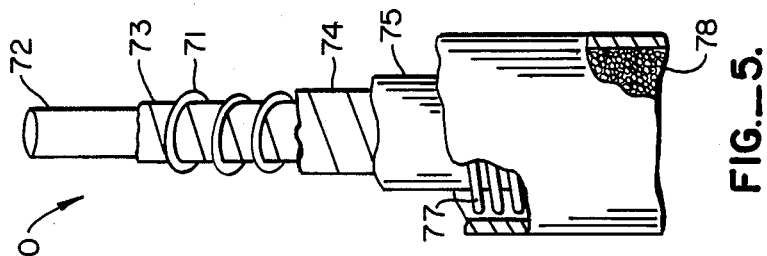
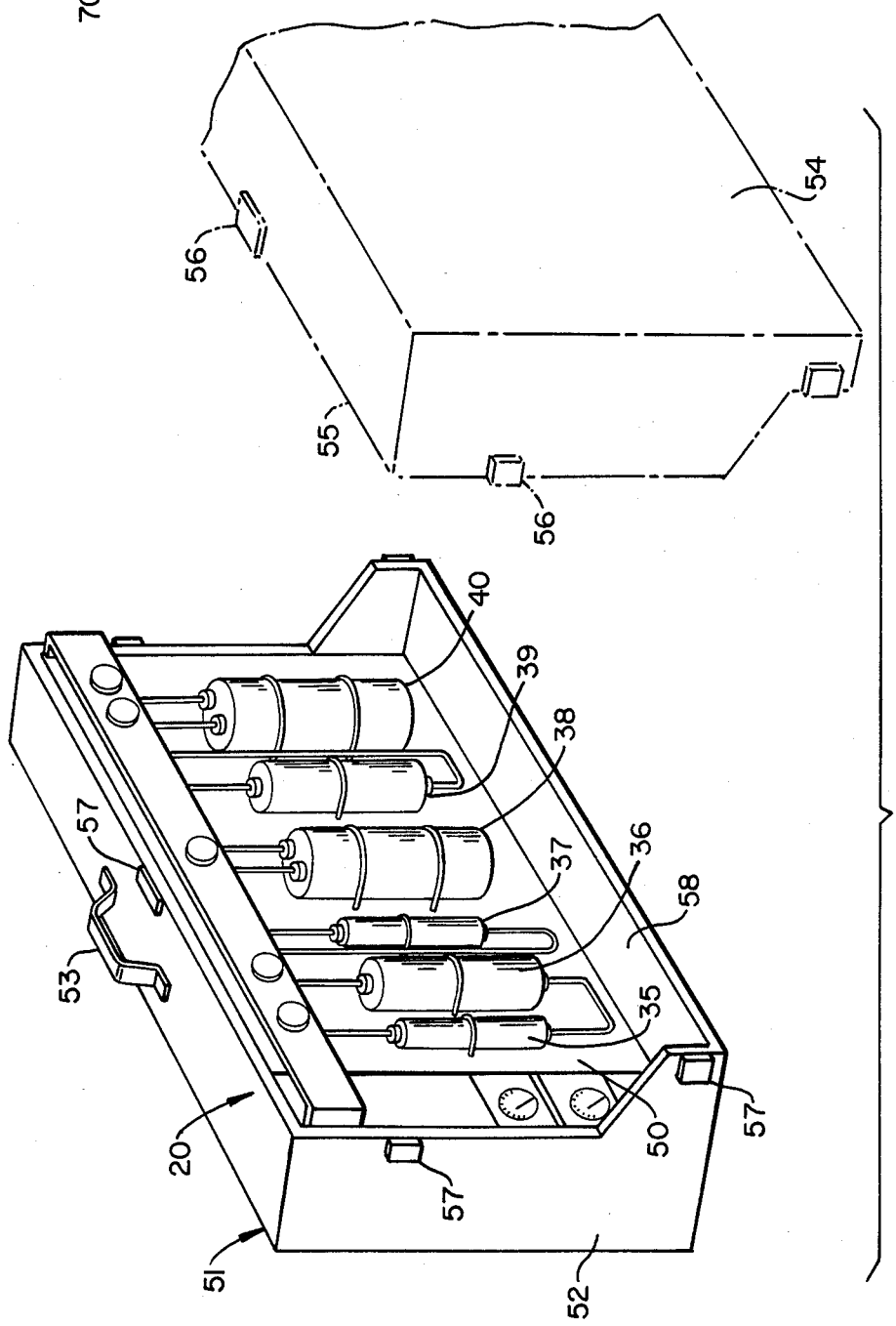

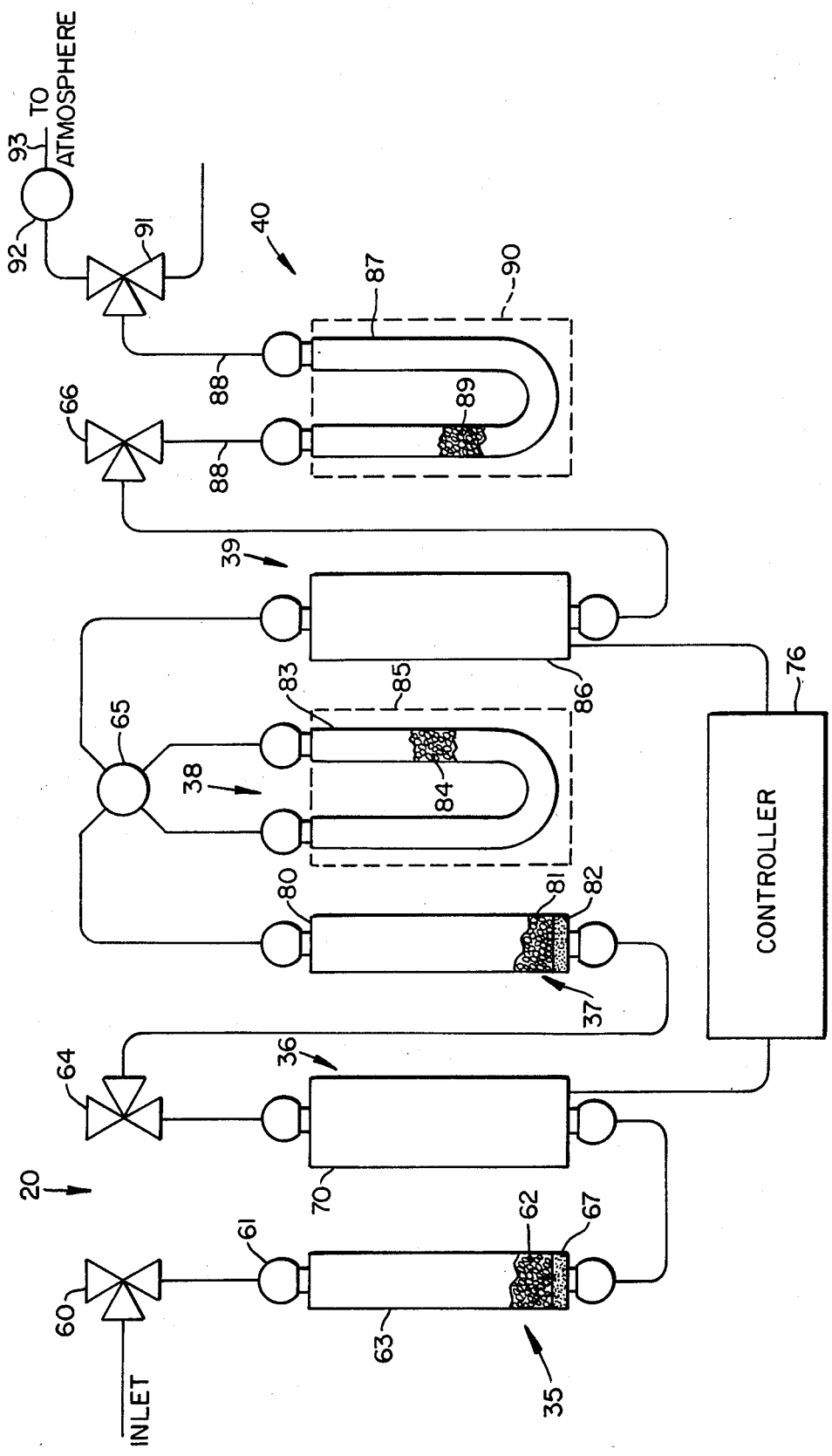
FIG._4.

CAPTURE BOX FOR PREDICTING HYDROCARBON POTENTIAL OF AN EARTH FORMATION UNDERLYING A BODY OF WATER

This is a continuation of application Ser. No. 353,760, filed Mar. 1, 1982, now abandoned.

SCOPE OF THE INVENTION

This invention relates to a method and apparatus—in general—for providing for isotopic chemical analysis of carbonaceous fluids from a hydrocarbon pool or other source of organic matter associated with an earth formation underlying a body of water, and—in particular—for providing for on-site capture of such fluids whereby indications of their biogenic and/or thermogenic origin can be accurately forecasted.

In one aspect, the present invention provides for the acquisition of highly accurate data related to the isotopic chemistry—and the biogenic and/or thermogenic origin—of extremely small concentrations of carbonaceous gases and oils, say 100 to 1000 microliter per liter of the sea water, being constantly collected at depth.

In another aspect, dissolved carbonaceous fluids including natural gases and oils are collectable in sufficient amounts utilizing vacuum separation and selective capture of natural gases utilizing an air carrier mixture. The sequence of steps includes: The fluids are first separated from the water collected at depth; then the methane present is quantitatively converted to carbon dioxide in the presence of a continuous air carrier vented to the atmosphere. Basis of later analysis is the isotopic composition of the $^{14}C$ or $^{13}C$ of the collected sample. Further, since the normalized variation of $^{13}C$ to $^{12}C$ (i.e., the delta $^{13}C$ measurement) requires less amounts of methane to be collected, such analytical method is preferred. The delta $^{13}C$ measurement is defined in *Petroleum Formation* and *Occurrence*, B. P. Tissot, D. H. Welte, Springer-Verlag, N.Y. (1978) at p. 88 as:

$$^{13}C^o/oo = \frac{(^{13}C/^{12}C) \text{ sample} - (^{13}C/^{12}C) \text{ standard}}{(^{13}C/^{12}C) \text{ standard}} \times 1000.$$

BACKGROUND OF THE INVENTION

While marine exploration systems are presently available for continuously sampling water seeps so as to analyze for presence of carbonaceous fluids such as methane, none have the capability of providing a compositional parameter that is uniquely diagnostic of seep origin, and hence allowing the user/operator to distinguish the biogenically derived sample from a sample associated with a thermogenic source.

Reasons: Other interpretative tests were thought to be sufficient from a cost/result standpoint. Also, the lengthy and complexed nature of the steps involved in collecting, isolating and tagging sufficient amounts of the samples for such analysis were thought to be beyond the capability of present on-site collection and analytical systems.

SUMMARY OF THE INVENTION

In accordance with the present invention, a quick, convenient and highly accurate technique for the acquisition of sufficient amounts of one or more carbonaceous constituents dissolved in sea water is provided. Result: Indications of the carbon isotopic character in the collected samples and of their biogenically- and/or thermogenically-derived origin, can be easily and suprisingly accurately determined.

In more detail, sea water is first collected via an electro-hydraulic cable, at depth by a drone trailing from a sea-going vessel, the water being pumped at a substantially constant flow rate in a range from about 3 to 7 liters/minute. Up cable destination of the water: A vacuum chamber aboard the vessel where the water is broken into droplets under a slight vacuum (27-28 inches of mercury) and the carbonaceous gaseous constituents, liberated. These constituents are carried via an air stream to a continuous hydrocarbon flame monitor where, if the flame monitor response is positive, more complexed analytical equipment is brought into play; e.g., a multiport valve can be energized as to allow the dissolved gases to be analyzed chromatographically. Or still another of the ports of the valve can be activated to allow the same constituents to flow into and through an isotopic trapping network where collection in microliter amounts occurs. Within the isotopic network, use is made of the flowing air stream (flow rate being preferably about 30 milliliters per minute in a range of 20-120 milliliters per minute). Gases of interest pass, in seriate, from station-to-station: Methane is isolated (by removing all interfering species), and finally converted to carbon dioxide (in a catalytically-aided oxidation reaction) and cryogenically trapped in a U-shaped trapping chamber. Next, the ends of the trapping chamber are heated and collapsed, sealing them from the atmosphere.

After being transported to a mass spectrometer, the chamber is re-opened so that isotopic analysis can occur. Using the latter results (along with geographic address data) allows for accurate biogenically- and thermogenically-associated predictions to be made. Basis: Delta $^{13}C$ values of each collected sample as a function of location.

DESCRIPTION OF THE DRAWINGS

FIG. 1 illustrates operation of the present invention, utilizing a vessel positioned on a body of water overlying an earth formation that collects and analyzes, continuously, samples of water at depth;

FIG. 2 is a schematic diagram of collection and analytical operations attendent on-site collection of water samples by the vessel of FIG. 1; and FIGS. 3-5 are detailed drawings of an isotopic capture network of the associated on-site collection and analytical operations of FIG. 2.

DETAILED DESCRIPTION OF THE PRESENT INVENTION

FIG. 1 illustrates the present invention.

As shown, a drone 10 is positioned at a depth $Z_0$ below a vessel 11 floating at the surface 12 of the body of water 13. Within the drone 10, is a pump (not shown). The purpose of the pump: To draw water samples interior of the drone 10 and pump them upcable (via electrohydraulic cable 14) to a diagnostic system 15 aboard the vessel 11.

In addition to pumping equipment, the drone 10 is fitted with various oceanagraphic devices, including a depth sensor; a current monitor is also provided that includes a bottom-oriented sonar device in combination with an electromagnetic sensor for measuring the speed and direction of the ocean currents relative to the bottom. Signals from these devices pass via conductors in the side walls of the cable 14 so as to provide annotation (both visual and on tape), associated with geographic position (of the drone and/or the vessel), depth of the drone, etc., as shown. In that way, accurate geographic addresses for the samples as a function of drone and/or vessel location, is assured.

Diagnostic system 15 also provides for a series of geochemical tests, and includes vacuum separation system 16 and a gas phase analysis network 17. Key to diagnostic results using network 17: determination that hydrocarbon gases are present and what types (using hydrocarbon analyzer system 18) in combination with a gas chromatagraph 19, and then isotopic examination via isotopic capture network 20.

FIG. 2 illustrates operation of diagnostic system 15 in still more detail.

As shown, vacuum separation system 16 includes an air-tight chamber 21 for separating the water into liquid and gas phases. Entry and egress from the chamber 21 via a series of inlets and outlets 21A–21C. Inlet 21A receives the water samples via cable 14 and associated manifold 22. A nozzle 24 breaks water into droplets. Note that even though the flow rate of the water can be as high as 7 liters per minute, usual flow rate is usually about 3.7 liters per minute. The separated liquid phase is discharged from the chamber 21 via outlet 21B and pump 25. The gas phase exits via outlet 21C through vacuum pump 26 and exhaust manifold 27 in the presence of a wet air carrier.

Also of importance in the operation of diagnostic system 15: storage and display of all annotation data via the electrical network/display 34 to allow for determination of geographic addresses of all samples taken by the drone, as previously explained.

Manifold 27 includes an arm 28 which terminates in a continuously operating hydrogen flame ionization analyzer 18. Remaining arm 29 of the manifold 27 terminates at multi-port valve 30.

One port 31 of the valve 30 is open to the atmosphere. Another port 32 is disconnectably connected to gas chromatagraph 19 which, when operating, providing gas chromatograms. Yet another port 33 of the valve 30 is disconnectably connected to isotopic capture system 20 of the present invention.

Since the gas chromatograph 19 as used in association with operations of the present invention is usual, that is, the gas chromatograph 19 provides chromatograms of hydrocarbon components in the water, emphasis of description is placed on isotopic analysis system 20 of the present invention.

FIG. 3 illustrates how easily isotopic capture system 20 can be transported aboard a vessel 11 in either an assembled or unassembled state and be effectively operated in any type of environment. And since all functions associated with the isotopic capture system 20 occur aboard a sea-going vessel often in a hostile environment, constructional aspects related to portability, reliability and ruggedness are of some importance.

As shown, the capture system 20 includes a series of trapping and stripping stations 35–40 mounted to upright front panel 50 of carry-on capture box 51. The box 51 includes side, top and back panels 52, which form an enclosure interior thereof, wherein equipment associated with operations can be stowed either temporarily as during transport (or permanently as required). Carry handle 53 facilitates hand-transport of the box 51 to and from the vessel. Note also that the front panel 50 intersects bottom panel 58 near its center. Hence, not only can the operator use bottom panel 58 as a floor for equipment associated with stations 35–40, but also he can place a separate cover 54 (shown in phantom line) in attachment with the panels 52, 58 as when transport of the box is required. In that way, the equipment comprising the stations 35–40 can be protected against breakage during transport. Note that the cover 54 has extending side and top panels 55 of reverse orientation with respect to the shape provided the side, top and bottom panels. Result: Disconnectably connecting hinges 56 can be aligned with mounts 57 to releaseably attach the cover 54 with respect to the panels 50, 52 and 58.

FIG. 4 illustrates operation of stages 35–40 of system 20 in more detail wherein such operations are carried efficiently, effectively and quickly without the need for substantial operator intervention.

Assume the operator has allowed dissolved gases to enter the sytem 20 via valve 60 to station 35 to begin operations.

The key to isotopic operation of system 20 lies in quantitative oxidation of the dissolved gases as within oxidation station 39 and subsequent collection at station 40. These operations occur after sinusoidal travel of the dissolved gases via the intermediate stations 35–38 as set forth below. The usual flow rate of the dissolved gases within system 20 is about 30 microliters per minute. The amount of collection at station 40 is dependent on the methane concentration in the sample sea water, the flow rate of the air carrier system, and the separation efficiency of the vacuum separation system aboard the vessel. If the normal methane concentration is 100 microliters per liter of water, and the extraction rate of the drone is 7 liters per minute at depth, then 2.28 seconds will be needed to collect 20 microliters of the gas of interest at station 40, assuming extraction efficiency at the vacuum system of 75%. In the vicinity of modest gas seeps, the concentration of methane can easily approach 1000 microliters per liter of water (STP) particularly in deep water.

Briefly with reference to FIG. 4, the wet air carrier and the dissolved gases from the vacuum separation center enters station 35 at inlet 61. At the station 35, the gases perculate downwardly through the series of absorbent materials 62 supported in upright tube 63. Materials 62 remove both water vapor and molecular carbon dioxide. Next, the carbon monoxide which also occurs in variable abundance in water, is removed at station 36 by oxidation to carbon dioxide; the latter is subsequently removed from the carrier system after passing via valve 64 to station 37. The carrier gas stream containing both air gases and low molecular weight alkanes is then directed to stage 38 after passage through valve 65.

At the station 38, the lower, mid- and higher-range molecular weight hydrocarbons are removed, that is, all hydrocarbons above $C_1$. The remaining methane then enters station 39 where is it oxidized to carbon dioxide. After passage through valve 66 the latter is subsequently retained at station 40. The details of operation of stages 35–40 will now be presented in more detail below.

STATION 35

Purpose: To trap water vapor and molecular carbon dioxide in the gas phase of the separated sample. The station 35 is constructed of the tube 62 attached to the front panel 50 of capture box 51 upright position, see FIG. 3, the tube 63 usually being constructed of standard wall pyrex tubing. A bed of absorbent materials 62 is held in place by small wads of glass wool 67 placed at the ends of the tube 63. The absorbent materials 62 are conventional and are available in the industry for removing water vapor (viz calcium chloride, $CaCl_2$) and for absorbing molecular carbon dioxide (namely, sodium hydroxide, $NA(OH)$). Mixture ratio 1:1.

STATION 36

Purpose: To remove carbon monoxide which occurs in variable amounts in sea water using a flow-through furnace system 70.

As shown in detail FIG. 5, furnace 70 consists of a helix 71 wound about a quartz tube 72, the tube being previously wrapped with a single layer of asbestos tape 73. The helix 71 is then covered with additional asbestos tape 74 as well as with a glass wool matting 75 forming a sidewall into which a thermocouple (not shown) can be inserted. The ends of the helix 71 and the thermocouple are electrically connected to thermal controller 76 of FIG. 4. The controller 76 supplies regulated power to the furnace as a function of temperature. At the remaining annular space between the sidewalls of the wool matting 75 and the exterior glass tube of the system 70 are positioned cupric oxide wire 77 along with platinized alumina pellets 78. The pellets 78 are placed at the downstream end of the tube 70, and held by quartz wool, not shown. The furnace operates about 125° C. whereby the carbon monoxide is oxidized to carbon dioxide.

STATION 37

Purpose: To remove carbon dioxide previously generated at station 36. Station 37 is constructed of a glass tube 80 filled with an absorbent material 81 such as sodium hydroxide, $Na(OH)$, held in place with glass wads 82, and is similar in construction to station 35 previously described.

STATION 38

Purpose: To remove lower-, mid- and high-range molecular weight hydrocarbons. Station 38 is constructed of a metallic tube 83 filled with inert chromatographic glass beads 84 in a size range of 60–80 mesh held in place by glass wool wads (not shown). When removal of low- mid- and high-range hydrocarbons is desired (removal of all hydrocarbons above $C_1$) a bath 85 consisting of liquid argon ($-180°$ C.) or isopentane-liquid nitrogen slush ($-160°$ C.) is placed circumferentially about the bed of beads 84.

If desired, station 38 can be by-passed via valve 65. Hence, clean-up of the tube 83 can be facilitated, i.e., a clean gas can be passed via valve 65 through the tube 83 while the bed of beads 84 is heated to a temperature of about 200°–300° C. for several minutes. Note that at temperatures above 400° C. however, the beads 84 will soften.

STATION 39

Purpose: To oxidize the methane of interest to carbon dioxide. The station 39 includes a furnace 86. It is similar in design and construction to the furnace 70 of station 36 shown in detail in FIG. 5, except that furnace 86 operates at temperatures in excess of 600° C. in a catalytically aided reaction. The temperature preferred is about 650° C. Result: methane is quantitatively converted to carbon dioxide at a lower operating temperature than would be normal, due in part to the effect of the cupric oxide helix and platinized alumina beads used as catalysts within the furnace 86. In this regard, it should be noted the combustion efficiency of the furnace 86 at different ranges and temperatures has been tested. A standard hydrocarbon mixture consisting of say 66 parts per million methane, 10 parts per million $C_2H_6$, 10 parts per million $C_3H_6$, and 10 parts per million $C_4H_{10}$ in a helium carrier, was passed through furnace 86 at 30 milliliters per minute. The test was repeated at 20 milliliters per minute. The vent of the furnace 86 was connected to a gas chromatograph equipped with a flame ionization detector. At the maximum sensitivity of the detector (approximately 0.5 parts per million $CH_4$ equivalent) with the above mixture flowing through the furnace 86 at the above rates, no methane was detected at the detector. The condition continued as long as combustion furnace 86 was above 600° C., say preferably 650° C. Larger amounts of methane were syringe-injected (say up to 400 microliters of methane) into the furnace with similar results. Thus, it is concluded that furnace 86 will quantitatively oxidize all methane concentrations that are likely to be obtained in the field.

STATION 40

Purpose: To trap microliter quantities of carbon dioxide oxidized at station 39.

Station 40 is constructed of a glass tube 87 bent into a U-shape. Its arms connect to transfer tubes 88 (and its inlet and outlet, respectively) which facilitate gas passage through the tube 87. The tube 87 is also filled with inert chromatographic grade glass beads 89 of average size, say 60–80 mesh forming a trapping bed. Beads 89 are held in place by wads of glass wool (not shown). Collection of the carbon dioxide is effected by immersing the tube 87 and beads 89 in a bath 90 of either liquid argon at $-180°$ C. or an isopentane-liquid nitrogen slush at $-160°$ C. Note that at the outlet of the station 40, the transfer tube 88 connects via valve 91 to either (i) flow meter 92 and vent 93 or (ii) to a vacuum pump (not shown). During collection, item (i), above, is connected to the tube 87. After the collection is complete, the valve 91 is operated to connect the interior of the tube 87 to the vacuum pump and the latter is turned on. The transfer tubes 88 are then sealed by heating them with a small oxy-propane torch. At a mass spectometer site, the contents of the tube 87 (carbon dioxide) and impurities, if they exist, (air gases, water vapor primarily) are introduced into a vacuum line where the carbon dioxide is purified prior to isotopic analysis. Prior to reusing the tube 87 and beads 89, both are heated to 200°–300° C. in the stream of clean air to remove organic contaminents. Note that cryogenic trapping by bath 90 can present some problems if the bath temperatures are not maintained with a range of $-160°$ to $-180°$ C. For example, it has been found that at higher temperatures (say $-125°$ C.) using an isopentane-liquid nitrogen slush, the carbon dioxide can break through the tube 87 to vent 93 at modest flow rates, say 16 milliliters per minute. At lower temperatures, say $-196°$ C., oxygen can condense on the beads 89 interrupting the carrier flow. Carbon dioxide has been found quantitatively to be retained on the beads 89 at $-160°$ C. using an isopentane-liquid nitrogen slush, for 25 minutes at flow rates of about 100 milliliters per minute.

Thus, at air carrier flow rates of 20–30 milliliters per minute, the carbon dioxide will be retained for periods of two hours or more. Moreover, at −180° C., the retention time of carbon dioxide will undoubtedly increase if liquid argon (−180° C.) is used.

EXPERIMENTAL DATA

An investigation of isotopic fractionation associated with system 20 of FIG. 4, has been undertaken, such investigation utilizing standard 5% methane-argon and 10% methane-argon mixtures. Results of isotopic examination are as set forth below in Table I.

TABLE I

| Sample # | Std | Vol. Inj. | Recovery % | $S^{13}C$ (PDB) $^\circ/_{oo}$ |
|---|---|---|---|---|
| HC-11 | 5% $CH_4$/Ar | 50 | 100 | −39.31 |
| HC-12 | 5% $CH_4$/Ar | 50 | 100 | −39.27 |
| HC-13 | 5% $CH_4$/Ar | 100 | 100 | −36.36 |
| HC-14 | 5% $CH_4$/Ar | 100 | 100 | −39.57 |
| HC-23 | 10% $CH_4/N_2$ | 100 | 100 | −26.07 |
| HC-24 | 10% $CH_4/N_2$ | 100 | 100 | −25.45 |
| HC-25 | 10% $CH_4/N_2$ | 100 | 100 | −25.53 |
| HC-26 | 10% $CH_4/N_2$ | 100 | 100 | −26.73 |
| Ref-1 | 10% $CH_4/N_2$ | — | 100 | −30.50 |
| Ref-2 | 10% $CH_4/N_2$ | — | 100 | −28.11 |
| Ref-3 | 10% $CH_4/N_2$ | — | 100 | −29.13 |

Samples HC-11 through HC-14 show good agreement and demonstrate a high level of precision at two concentration levels of 50 microliters and 100 microliters of the carbon dioxide (STP). Mean and standard deviations of the delta $^{13}C$ composition were −39.38±0.13. Reference samples have not yet been analyzed.

Samples HC-23 through HC-26 and reference samples 1-3, provide similar results except the delta $^{13}C$ distributions were systematically "lighter" by a value of −3.57°/$_{oo}$. There is, at present, no explanation for the systematic bias noted above.

In a parallel study, sea water saturated with a methane/argon mixture at two temperatures (18 C.° and 2° C.) was stripped of its dissolved methane. The dissolved methane was then condensed to carbon dioxide at an air carrier flow rate of 30 milliliters per minute. Approximately 30% of the methane was removed from solution in 10 minutes. Results of isotopic examination are set forth below with reference to Table II.

TABLE II

| Sample # | Std | Vol. Inj. | Recovery % | $S^{13}C$ (PDB) $^\circ/_{oo}$ |
|---|---|---|---|---|
| HC-15 | 5% $CH_4$/Ar | 1495$^a$ | 32 | −40.16 |
| HC-19 | 5% $CH_4$/Ar | 2180$^a$ | 30 | −39.17 |

$^a$saturation concentrations in 1 liter sea water at 18° and 2° C.

Note that samples HC-15 and HC-19 represent partially stripped sea water previously equillibrated with the 5% methane/argon mixture, the same mixture used to obtain the results in Table I. But also note that the results of Table II are not significantly different than those obtained for samples HC-11 through HC-14 of Table I which were achieved using the same source tank of methane/argon. Of particular interest in Tables I and II, is the fact that the fractionation associated with incomplete stripping of the samples HC-15 and HC-19 in Table II is less than 1°/$_{oo}$. This is expected since the fractionation factor is about 1.03 (or the square root of 17/16). That is to say, for small methane stripping efficiencies (less than 1%), the resulting carbon dioxide will be 3°/$_{oo}$ lighter than the parent methane. At 30% recoveries, the fractionation is within experimental error.

Isotopic fractionation is dependent on vapor pressures of $C_{12}H_4$ and $C_{13}H_4$, each of which being temperature dependent. At temperature extremes likely to be encountered at the surface of the earth (−2° C. to 45° C.), isotopic fractionation associated with gas extraction should be within experimental error. It is also worth noting that success of the present invention does not depend on the absolute delta $^{13}C$ values provided for either the biogenic or thermogenic methane fractions. Relative changes in a local region are the focus of interest.

From the above, it is apparent from the invention as herein before described that variations are readily apparent to those skilled in the art, and hence the invention is not limited to combinations herein before described but should be given the broadest possible interpretation in terms of the following claims:

What is claimed is:

1. Portable capture box for on-site capture of the combustion product, carbon dioxide, of methane dissolved in a gas stream vacuum separated from a stream of water taken from a body of water at a known-on-site location by vacuum separator means aboard a vessel at the surface of said body of water so that accurate predictions of hydrocarbon potential of an earth formation underlying the body of water from which said methane was collected, can be made based on carbon isotope concentration in the carbon dioxide comprising:

a support box including a separately detachable side cover means adapted to be carried aboard said vessel in a transport mode, by carrying means attached to a wall of said support box, wherein a series of interconnected trapping, stripping and combustion stations each of which being of an elongated configuration, are fixedly attached at a central wall member of said box adjacent to but interior of closure surfaces formed between said box and said side cover means whereby said series of stations are protected from breakage during said transport mode, said support box also being capable of operating in an isotope capture mode after said side cover means has been detached from said support box wherein said box is placed atop a suitable horizontal support means on said vessel, said side cover means including releasable attaching means for disconnectably connecting said cover means to said box, said cover means also having elongated side, top and bottom walls extending from a front wall to define a storage compartment therein that extends about said series of stations for protection thereof during said transport mode but being easily releasable when isotope capture operation is contemplated wherein said series of stations attached to but facing outwardly from said central wall member of said support box, are exposed for easy servicing and viewing by a human operator, valve means connectable to a separator means aboard said vessel so that said operator can connect said series of stations thereto in said isotope capture mode wherein said gas stream from said separator means is serially directed through said series of stations in a continuous flow pattern for selective stripping and combusting of said methane to carbon dioxide and capturing of said carbon dioxide, without substantial operator intervention, said stations each having an inlet and an outlet and in combination including a first tube packed with absorbent material for water vapor and carbon dioxide and a first oxidation furnace located adjacent thereto for converting carbon monoxide to carbon dioxide, said first tube having its outlet connected to the inlet of said first oxidation furnace, a second tube packed with absorbent material for carbon dioxide having its inlet connected to the outlet of said first oxidation furnace, a first capture tube filled with glass beads at dry ice temperature for removal of lower-, mid- and high-range molecular weight hydrocarbons having its inlet connected to the outlet of said second tube packed with absorbent material, a second furnace having for converting methane to carbon dioxide, said furnace having its inlet connected to the outlet of said first capture tube and a second capture tube also filled with glass beads at dry ice temperature for trapping carbon dioxide having its inlet connected to the outlet of said second furnace whereby said stations provide trapping, stripping and combustion of said stream of gas passing through said stations in sinusoidal flow pattern during said isotope capture mode.

2. Said box of claim 1 in which each of said series of stations define an axis of symmetry that is substantially vertical to said horizontal support means during both said isotope capture operation and said transport mode.

* * * * *